(12) United States Patent
De Boer et al.

(10) Patent No.: US 6,208,415 B1
(45) Date of Patent: Mar. 27, 2001

(54) BIREFRINGENCE IMAGING IN BIOLOGICAL TISSUE USING POLARIZATION SENSITIVE OPTICAL COHERENT TOMOGRAPHY

(75) Inventors: Johannes F. De Boer, Irvine, CA (US); Thomas E. Milner, Austin, TX (US); J. Stuart Nelson, Laguna Niguel, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/096,434

(22) Filed: Jun. 11, 1998

Related U.S. Application Data (60) Provisional application No. 60/049,371, filed on Jun. 12, 1997.

(51) Int. Cl.[7] .................................................... G01B 9/02
(52) U.S. Cl. .......................................... 356/351; 356/345
(58) Field of Search .................................. 356/351, 345, 356/365

(56) References Cited

U.S. PATENT DOCUMENTS

| | | |
|---|---|---|
| 5,202,745 | 4/1993 | Sorin et al. . |
| 5,321,501 | 6/1994 | Swanson et al. . |
| 5,459,570 * | 10/1995 | Swanson et al. .................... 356/345 |

* cited by examiner

Primary Examiner—Robert H. Kim
Assistant Examiner—Andrew H. Lee
(74) Attorney, Agent, or Firm—Daniel L. Dawes (57) ABSTRACT

Employing a low coherence Michelson interferometer, two dimensional images of optical birefringence in turbid samples as a function of depth are measured. Polarization sensitive detection of the signal formed by interference of backscattered light from the sample and a mirror or reference plane in the reference arm which defines a reference optical path length, give the optical phase delay between light propagating along the fast and slow axes of the birefringence sample. Images showing the change in birefringence in response to irradiation of the sample are produced as an example of the detection apparatus and methodology. The technique allow rapid, noncontact investigation of tissue or sample diagnostic imaging for various medical or materials procedures.

33 Claims, 7 Drawing Sheets

BIREFRINGENCE IMAGING IN BIOLOGICAL TISSUE USING POLARIZATION SENSITIVE OPTICAL COHERENT TOMOGRAPHY

RELATED APPLICATIONS

The present application is a continuation in part of provisional application Ser. No. 60/049371 filed on Jun. 12, 1997 entitled Two Dimensional Birefringence Imaging And Biological Tissue Using Polarization Sensitive Optical Coherence Tomography.

This invention was made with government support under Grant No. DE-FG03-91ER61227 awarded by the Department of Energy and Grant Nos. AR42437, AR41638 and RR01192 awarded by the National Institutes of Health. The government has certain rights in this invention.

BACKGROUND OF THE INVENTION

1. Field of the Invention

The invention relates to the field of optical imaging and in particular to the use of optical polarizations to create tomographic images.

2. Description of the Prior Art

The demand for noninvasive optical images of biological tissue has led to the development of several techniques to circumvent the common problem of scattering in turbid media. Such techniques include diffusing wave spectroscopy A. Yodh, et al., "*Spectroscopy and Imaging with Diffuse Light,*" Physics Today 48, 34 (1995); F. Liu, et al., "*Transmitted Photon Intensity through Biological Tissues within Various Time Windows,*" Opt. Lett. 19, 740 (1994); W. Denk, et al., Handbook of Biological Confocal Microscopy, edited by J. B. Pawley (Plenum New York 1995) at p445; L. Wang, et al. "*Continuous-Wave Ultrasonic Modulation of Scattered Laser Lidght to Image Objects in Turbid Media,*" Opt. Lett. 20, 629 (1995); M. Kempe, et al., "*Acousto-optic tomography with Multiple Scattered Light,*" J. Opt. Soc. Am. A14 (1997); and D. Huang, et al. "*Optical Coherence Tomography*", Science 254, 1178 (1991); and A. F. Fercher, "*Optical Coherence Tomography*", J. Biomed. Opt. 1, 157 (1996).

Optical coherence tomography employs the partial coherence properties of a light source to image structures with high resolution, namely, in the range of one to fifteen microns, in turbid media such as biological tissue. The sample under study is positioned in one arm or sample arm of a two beam interferometer. The interference fringes are formed when the optical path length of the signal back scattered from the sample matches that from the reference arm to within the coherence length of the source light. The optical path length in the reference arm acts as a detection gate to thereby select only light back scattered from the sample that has traveled the same optical path length. By laterally and longitudinally scanning the sample, two dimensional optical coherence tomographic images are constructed that map the amplitude of light back scattered from the sample. Lateral resolution is determined by the spot size of the beam focus of incoming light and the collection aperture. Longitudinal resolution is determined by the coherence length of the source light.

Optical coherence-domain reflectometry is further described by Sorin, et al. "*Polarization Independent Optical Coherence-Domain Reflectometry,*" U.S. Pat. No. 5,202,745 (1993). Sorin describes the use of an incoherent light source in an interferometer in which the reference mirror is moved at a controlled velocity to produce a Doppler shift in the reference signal in the interferometer. The phase of the reference signal is also modulated by piezo-electric transducer to cause a further shift in the referenced signal frequency. The interference signals are detected and measured by a polarization diversity receiver. A linear polarizer and reference signal arm is adjusted to produce equal reference signal powers in each arm of the polarization diversity receiver in the absence of reflection signal from the test arm. The measured reflectometry signal is substantially independent of the state of polarization and the reflected signal from the device under test. The system is generally used to test the optical properties of optical fiber systems. Polarization stability can be a problem in such testing situations. Sorin is directed to a methodology to overcome the problem of polarization variations and distortions in optical fibers and system components. Sorin thus describes the system in which the polarization information returned from the sample or test object is treated as noise and is effectively disregarded.

Prior art examples of the use of optical coherence domain reflectometry is described in Swanson, et al. "*Method and Apparatus for Performing Optical Measurements,*" U.S. Pat. No. 5,459,570 (1995). The use of the method for performing optical imaging and sample using longitudinal scanning and positioning of a sample by varying the relative optical path lengths leading to the sample into a reference reflector or by varying the optical characteristic of the output from the optical source is shown and described in Swanson, et al., "*Method and Apparatus for Optical Imaging with Means for Controlling the Longitudinal Range of the Sample,*" U.S. Pat. No. 5,321,501 (1994).

Swanson '570 and '601 describes inter alia a system in which birefringence information may be obtained by polarizing the optical radiation used, by suitably modifying the polarization in the sample and reference paths, and by dividing the output into an orthogonal polarization outputs which are separately demodulated before processing. In particular, in FIG. 6 in Swanson '570 orthogonal polarized back scattered interference fringes are provided to two separate detectors 42C and 42D into a beam splitter in the return arm of an interferometer using a coherent light source 12 as the interferometer source signal. The interferometric signals detected by detectors 42C and D are separately processed in demodulators 46 and A-to-D converters 50 to produce two interferrometric signals, a horizontal amplitude component 11 and a vertical amplitude component 12. These signals are applied to computer 52 and used to determine the round trip birefringence retardation in the sample like path. Swanson does not in fact measure the phases from two detector outputs. The relative phase information is computed from measured amplitudes of the two orthogonal components under a set of special assumptions. In order to obtain computed phase information from the signals in Swanson, the optical birefringence axes in the sample must be constant.

Demodulator 46 for each of the signals is detailed further in FIG. 2. Demodulator 46 is comprised of a band pass filter 78 centered around the modulation frequency of the combined output signal and an envelope detector. The filter assures that only the signal of interest is looked at and removes noise from the output. The filter signal is applied to the envelope detector. The envelope detector is comprised of a rectifier 82 and a subsequent low pass filter 84. The rectifier output is proportional to the square of the sample reflectivity. The low pass filter removes any high frequency components from what is basically a base band signal.

Demodulator 46 also includes a logarithmic amplifier 86 for dynamic range compression.

The effect of rectification of the signal is graphically illustrated by a comparison of FIGS. 5A and 5B. FIG. 5A illustrates the output waveform modulation frequency on which the envelope is superimposed. FIG. 5B is the wave form of FIG. 5A after demodulation by demodulator 46. Thus, it is clear from Swanson that the information contained within the fringes or oscillations of FIG. 5A are lost in the demodulation. As will be described below, it is this information in the undemodulated signal of Swanson that provides a basis when used according to the invention to develop a two dimensional birefringence imaging signal, and more generally create a polarization sensitive optical coherence tomograph using spatially resolved Stokes parameters of the backscattered light from highly scattering biological samples.

Many surgical procedures use laser radiation to selectively photocoagulate subsurface chromophores in biological tissue in order to obtain a desired therapeutic effect. What is needed is the diagnostic imaging system to provide real-time feedback control for optical laser dosimetry. Application of surgical techniques using radiative energy to selectively destroy chromophores in tissue is limited by the availability of feedback techniques for real-time control of the laser dosimetry. A generic radiative treatment apparatus consists of a generic radiative treatment apparatus and is comprised of five major subsystems, namely (1) a radiative source such as a laser; (2) a diagnostic imaging subsystem; (3) image processing and analysis subsystem; (4) a feedback control subsystem; and (5) a delivering device which delivers the radiative energy to the sample.

Two non-contact methods have been proposed and tested as diagnostic imaging techniques for use in a generic radiative treatment apparatus. These methods include infrared imaging radiometry and polarization sensitive detection of the remitted backscattered light intensity. Both techniques are limited by poor spatial resolution of the inferred structural changes in the tissue which is induced by the incident radiation.

Infrared imaging radiometry uses a detector to measure temperature rises in a tissue induced by pulsed laser radiation. The temperature rise due to selective optical absorption of pulse laser light, creates an increase in infrared blackbody emission which is measured by the detector. Because biological materials are composed primarily of water, blackbody emission from tissue originates from a thin 5 to 50 $\mu$m superficial layer on the tissue surface. Therefore, infrared imaging radiometry provides little useful information in the temperature distribution and result in structural changes at deep positions in the irradiated tissue. Furthermore, because the transport of thermal energy from deep portions to the tissue surface is a diffusive process, determination of underlying tissue changes is an ill-posed inverse problem that requires application of a computational algorithm to analyze the time sequence of infrared emission images. The ill-posed nature of the problem places severe limitations on the spatial resolution that can be realized from measurements through infrared imaging radiometry.

Polarization sensitive detection of remitted backscattered light intensity has recently been proposed as a non-contact imaging technique to monitor changes and tissue birefringence during laser irradiation. This technique relies on changes and the birefringence of native collagen in tissue upon exposure to laser irradiation. As collagen is subjected to higher temperatures over prolonged times, the molecular helix begins to unwind and birefringence is lost. If incident diagnostic light is linearly polarized, detected intensity changes of the remitted backscattered light from the tissue in the orthogonal polarization mode may indicate partial loss of collagen birefringence. Although this technique has been demonstrated to provide an average measure of bulk tissue birefringence changes, spatially resolved measurements have not been possible. Because this technique does not discriminate between the multitude of optical paths contained in remitted backscattered light from the tissue, spatial resolution in the lateral and longitudinal directions is limited by, respectively, the scattering anisotropy coefficient and the optical penetration depth. In the visible near infrared spectral regions, lateral and longitudinal spatial resolution is approximately 500 $\mu$m.

BRIEF SUMMARY OF THE INVENTION

The invention is an apparatus for polarization sensitive optical coherence tomography of a sample characterized by optical birefringence comprising an interferometer having a source arm, a reference arm, a sample arm and a detector arm. A source of at least partially coherent polarized light is coupled to the source arm. A polarization modulator is provided, typically in the reference or sample arm. The polarization modulated light is returned to the detector arm from the reference arm and is incident on the sample. Arbitrarily polarized light is returned to the detector arm from the sample arm according to sample birefringence. The returned light from the reference arm and sample arm interfers in the detector arm. A polarization demodulator demodulates the polarization modulated interference fringes to generate a complete polarization state description of the backscattered light from the sample.

The apparatus further comprises a scanner for laterally moving the sample and the sample arm relative to one another transverse to the longitudinal direction along which the light is incident on the sample, and for longitudinally moving the sample and sample arm relative to one another to obtain a two dimensional image of the sample.

In the illustrated embodiment the polarization modulator circularly polarizes orthogonal states of the polarization modulated light. The polarization modulator may generate either uniformly or nonuniformly rotating linear polarized light to be returned to the detector arm from the reference arm. In the illustrated embodiment an uniformly rotating quarter wave plate rotates linearly polarized light in the reference arm. The polarization modulator rotates linearly polarized light in the reference arm through at least part of the Poincare sphere. In another embodiment the polarization modulator comprises an electro-optical variable waveplate. The type of polarization modulation which may be used is, however, completely arbitrary and must be understood to be completely general in its scope.

In a first embodiment the polarization demodulator comprises a single detector which detects polarization modulation of the polarization modulated light to obtain relative phase differences between orthogonal components of the polarization modulated light. In a second embodiment the polarization demodulator comprises two detectors. Each of the two detectors detects over time a separate orthogonal component of the polarization modulated light to obtain a complete set of polarization states of the Poincare sphere sufficient to determine orientation of optical axes of the sample and birefringence of the sample.

The polarization demodulator averages the demodulated, orthogonal polarization states of interference fringes according to a weighted average to obtain a value for a pixel image.

The apparatus further comprises a rapid spectral optical delay line to provide for longitudinal scanning of the sample. In this case the apparatus further comprises a phase modulator in the sample arm or reference arm to decouple longitudinal scan speed and modulation frequency of the rapid spectral optical delay line.

In one embodiment the demodulator generates the Stokes parameters, I, Q, U, and V and the degree of polarization, P, from the orthogonal signal components of the intensity of backscattered light from the sample. The invention is also defined as a method for performing polarization sensitive optical coherence tomography of a sample characterized by optical birefringence comprising the steps of providing a source of at least partially coherent light coupled to an interferometer having a source arm, a reference arm, a sample arm and a detector arm. The light is polarization modulated in at least the reference arm or sample arm. Polarization modulated partially coherent light is returned to the detector arm from the reference arm and the sample arm. The polarization modulated partially coherent light is incident on the sample and arbitrarily polarized light is returned to the detector arm from the sample arm according to sample birefringence. The returned light from the reference arm and sample arm interferes in the detector arm to coherently gate the returned light from the sample arm in the detection arm in order to select between a multiplicity of optical paths of backscattered light returned from the sample arm. The polarization modulated interference fringes are demodulated in the detector arm to provide a data signal indicative the optical birefringence of the sample.

The step of providing the source of polarization modulated partially coherent light comprises in one embodiment uniformly or nonuniformly rotating the linearly polarized partially coherent light in the reference arm or sample arm.

The step of demodulating phase sensitive, orthogonal polarization states of the interference fringes in the detector arm to provide a data signal indicative the optical birefringence of the sample further comprises the step of generating the Stokes parameters, I, Q, U and V from the orthogonal signal components of the intensity of backscattered light from the sample to provide a complete polarization state description of the backscattered light from the sample.

The invention is more generally defined as a method for performing polarization sensitive optical coherence tomography of a sample characterized by optical birefringence comprising the steps of generating two polarization-modulated orthogonal polarization states of an at least partially coherent light signal. Interference fringes of two polarization-modulated orthogonal polarization states are generated from a reference signal and a backscattered sample signal. The fringes have an amplitude and relative phase with respect to the other modulated orthogonal polarization state for each of the two polarization-modulated orthogonal polarization states. The amplitude and phases of the interference fringes of the two polarization-modulated orthogonal polarization states are measured. The amplitude and phases of the interference fringes of the two polarization-modulated orthogonal polarization states are polarization demodulated to obtain the full polarization state of the backscattered sample signal to obtain structural information pertaining to the sample.

The invention and its various embodiment as briefly summarized above can be better visualized by turning to the following drawings wherein like elements are referenced by like numerals.

BRIEF SUMMARY OF THE DRAWINGS

FIG. 2b is a computer tomograph birefringence of laser radiated bovine tendon shown in FIG. 2a.

The invention now having been illustrated in the foregoing drawing can now be better understood by turning to the following detailed description of the preferred embodiments.

DETAILED DESCRIPTION OF THE PREFERRED EMBODIMENTS

The present invention combines optical coherence tomography (see M. R. Hee, et al., J. Opt. Soc. Am. B9, 903 (1992)

with polarization sensitive detection to record two dimensional images of the change of polarization of circularly polarized incoming light which is backscattered from a turbid birefringent sample, typically a biological sample. In contrast with conventional optical coherence tomography where the magnitude of the backscattered light is imaged as a function of depth, backscattered light is used in the invention to image the magnitude of the birefringence in the sample as a function of depth. Two dimensional maps of the optical birefringence of biological materials reveal important structural information in the biological sample that is otherwise difficult to resolve using other imaging techniques. For example, partial loss of birefringence is known to be an early indication of thermal damage in tissue such as in burns or laser treatments.

It will demonstrated below that polarization sensitive optical coherence tomography of the invention reveals structural information on birefringent turbid media, such as biological tissue, which is not available when using polarization insensitive optical coherent tomography. Polarization sensitive optical coherent tomography has potential to provide guidance regarding optical dosimetry for thermally mediated laser therapeutic medical procedures by allowing real-time diagnosis at each irradiated sight through detection of changes in the sample birefringence associated with thermal damage at pathological condition. This permits semi-quantitative evaluation of the efficacy of laser therapy as a function of the incident light dosage.

Thus, it is understood that polarization sensitive optical coherence tomography as disclosed herein can be employed for real-time diagnostic imaging for surgical procedures in general. Surgical procedures involve the use of several types of energy and techniques to modify biological tissues to obtain the desired therapeutic effect. For example, mechanical, acoustical, thermal, cryogenic and radiative electromagnetic energy sources can be applied while schemic and pharmacological techniques practiced. In all procedures, real-time feedback on the induced changes in tissue would be extremely useful to the procedure. What is described here is a polarization sensitive optical coherent tomographic system 10 for use as a diagnostic imaging subsystem in a generic treatment apparatus. Although the illustrative embodiment is described in a context thermally mediated laser surgery, the invention is not limited to this application but may be applied to any tissue mediation procedure or system.

The present invention uses a coherence gate to discriminate between the multitude of optical paths contained in the diagnostic light backscattered from a tissue to substantially improve spatial resolution of birefringence changes caused by higher temperatures. Lateral and longitudinal spatial resolution of polarization sensitive optical coherence tomography is limited by, respectively, the numerical aperture and the coherence length of the source light which in practice is about 2–15 $\mu$m.

The details of specific implementation of polarization sensitive optical coherence tomography are described below. First, consider the apparatus as diagrammatically shown in FIG. 1. Interferometer system 10 uses a partially coherent light source 12, such as a super luminescent diode having a linearly polarized output. In the illustrated embodiment light source 12 has an output of 0.8 mW at a wave length of 856 nm with a spectral full width half maximum of 25 nm. Light from diode source 12 passes through a Glan-Thompson polarizer 14 which selects a pure linear vertical input state. Light is then spread by a beam splitter 16 into a reference arm 18 and sample arm 20 of a Michelson interferometer.

Figure 1:
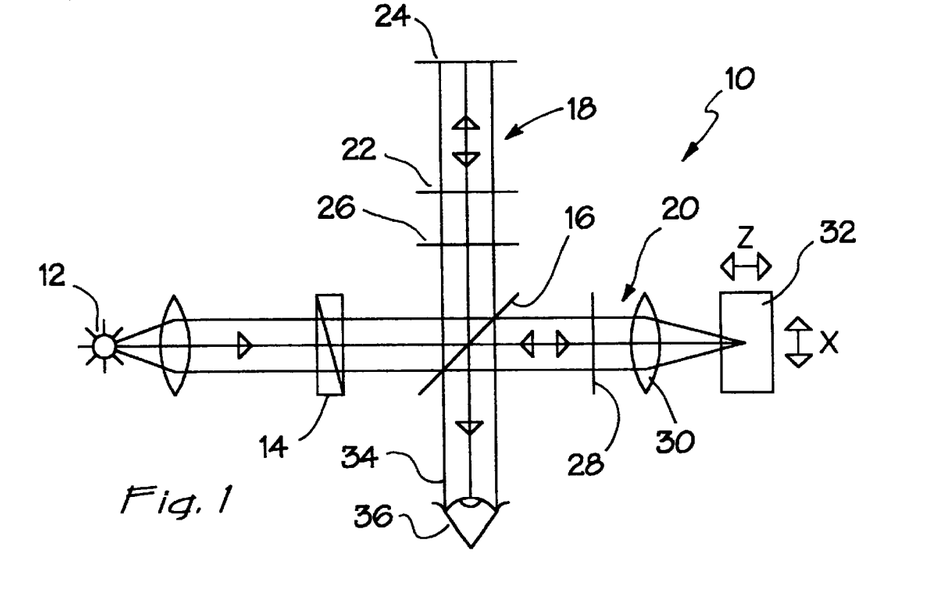
FIG. 1 is a diagram of an apparatus or interferometer system in which the invention may be practiced.

Beam splitter 16 has a reflection and transmission coefficient for linear vertical and horizontal polarization states of 0.5±0.05. Light in reference arm 18 passes through a zero order quarter wave plate 22, which quarter wave plate 22 rotates the light at a rate of 200 $\pi$ radians per second. To measure the relative phases of the two orthogonal polarization components, the rotation rate of the linear polarization due to the quarter wave plate must exceed the frequency generated by relative changes in the optical path lengths of the sample and reference arms, such as due to the longitudinal scanning of the sample. Accuracy of the relative phase measurement increases as the frequency separation between the rotation rate of the quarter wave and the frequency generated by relative changes in the optical path lengths of the sample and reference arms increases. Light impinges upon a planar mirror 24 and makes a return pass through quarter wave plate 22. Light in reference arm 18 therefore has a rotating linear polarization of 400 $\pi$ radians per second. Improvement of the signal-to-noise ratio is obtained by a neutral density filter 26 which is placed in reference arm 18 to reduce intensity of the noise by a factor of 50. Light split by beam splitter 16 into sample arm 20 passes through a quarter wave plate 28, oriented at 45° to the incident vertical polarization, to give circularly polarized light. The circularly polarized light from quarter wave plate 28 is focused by lens 30 to a spot size of 17 microns in diameter on sample 32. In the illustrated embodiment the focal length of lens 30 is 50 millimeters. Backscattered light from sample 32 passes again through lens 30 and quarter wave plate 28 to result in light with an elliptical polarization state as determined by the sample birefringence properties.

Figure 3:
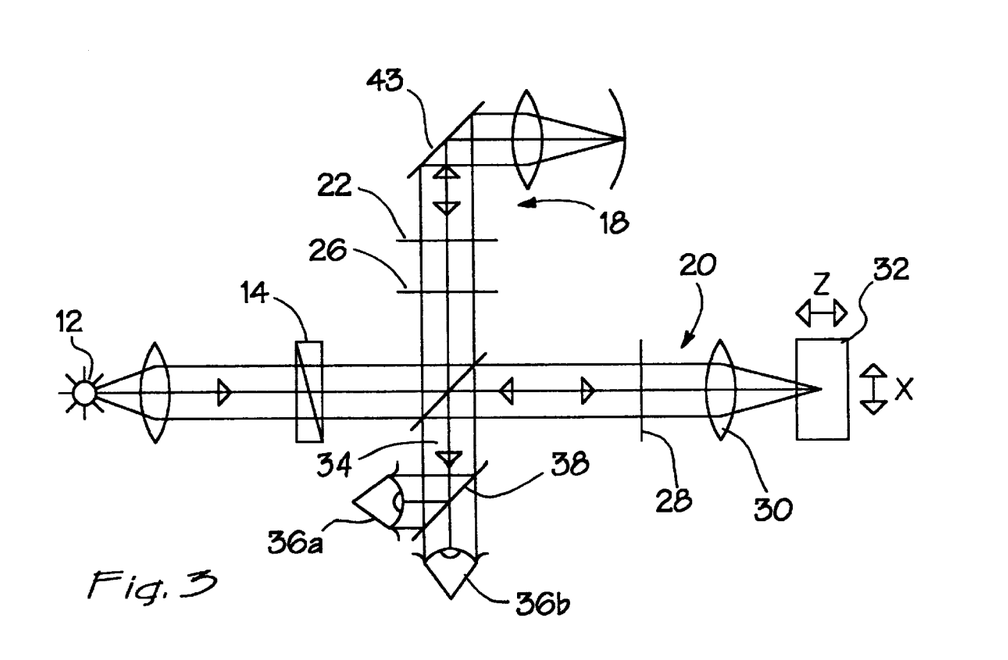
FIG. 3 is a diagram of a second embodiment of the apparatus of FIG. 1 wherein the polarization states of the detected signal are separately detected.

Light from reference arm 18 and sample arm 20 are then recombined in detection path 34. In the illustrated embodiment of FIG. 1 the combined light then impinges upon detector 36. In the second embodiment of the invention such as shown in FIG. 3, detector 36 is replaced by detectors 36A and 36B to which polarized light in detection arm 34 is split by a polarizing beam splitter 38 and focused on a 25 micron diameter pin hole placed directly in front of detectors 36A and 36B to detect a single spatial mode as described below. It should be understood that detector 36 or 36A and B as appropriate, are coupled to appropriate signal conditioning and data processing circuits or computers (not shown) which perform the data reductions required by the equations set forth in this specification according to well known means. Therefore, the term "detectors" or "demodulators" is to be understood not only to include optical detection devices and circuits, but to also include demodulation and data processing circuits and software controlled processors as may be required from context.

Returning to the embodiment of FIG. 1 the intensity of detector 36 is given by recombination of the light in both arms 18 and 20 of interferometer 10 is given by equation 1 below.

$$\langle I \rangle = \langle I_r \rangle + \langle I_s \rangle + 2Re[\langle \vec{\Psi}_r^*(t,z_r) \cdot \vec{\Psi}_s(t,z_s) \rangle] \quad (1)$$

Where $\vec{\Psi}(t,z)$ is the light amplitude field vector, subscripts r, s, denote the reference and sample arms respectively, the $z_{r,s}$ are the optical path lengths of the same, and angular brackets denote ensemble averaging. The source spectral density S ($\omega$) is assumed to be Gaussian, that is proportional to $\exp[-(\omega-\omega_0)^2/\Omega^2]$ with a full width half maximum of $2\Omega\sqrt{\ln 2}$ rad/sec, where $\Omega$ is the optical bandwidth of the source. The evolution of the polarization state in each arm 18 and 20 of interferometer 10 is computed using the Jones Matrix formalism where optical dispersion in the sample and spectral dependence of the zero order quarter wave plates 22 and 28 over the spectrum of source 12 is ignored. The interference intensity between light in sample path 20 and reference path 18 can be separated into horizontal $A_H$ and vertical $A_V$ components that are proportional to the light amplitude fields backscattered from sample 32 as given by equations 2 below.

$$Re[<\vec{\Psi}_r^*(t,z_r)\cdot\vec{\Psi}_{rs}^*(t,z_{sr})>]=A_H+A_V;$$
$$A_H \approx \sin(2\dot{\Theta}t)\cos(2k_0\Delta z)e^{-(\Omega\Delta z/c)^2}\cos(k_0\delta),$$
$$A_V \approx \cos(2\dot{\Theta}t)\cos(2k_0\Delta z+2\alpha)e^{-(\Omega\Delta z/c)^2}\sin(k_0\delta), \quad (2)$$

$\Delta z$ is the optical path link difference between sample arm 20 and reference arm 18 of interferometer 10. In the apparatus of FIG. 1, $\Delta z$ is a function of time and longitudinal velocity of sample 32, z is the backscattered depth within sample 32, $k_0=2\pi/\lambda_0$, c the speed of light in the vacuum, $\delta$ the difference in refractive indices along the fast and slow axis of the birefringent $(n_s-n_f)$, and $\Theta$ is the rotation speed of quarter wave plate 22 in reference arm 18 and $\alpha$ is the angle of the fast optical axis of birefringent sample 32 with the horizontal. The only approximation in equation 2 above is that of the product of birefringence and propagation depth in sample 32, which in the illustrated embodiment was $z\ \delta \leq 2.6$ microns, which is much smaller than the width of the coherence envelope, which again in the illustrated embodiment was $2c/\Omega=19$ microns.

Phase sensitive demodulation of the recorded signal in detector 36 with respect to the modulation of the polarization, namely the angular position, $(\dot{\Theta}t)$, of the rotating quarter wave plate 22, allows separation of the signal amplitudes of the vertical and horizontal polarized light components. In addition to the carrier frequency of $2k_0\Delta z$ within the coherence envelope, $\exp[-(\Omega\Delta z/c)^2]$, both signals show an oscillation with a periodicity determined by the product of sample birefringence, $\delta$, and the propagation depth, z, that allows for birefringent imaging.

Scans are made by moving sample 32 at a constant velocity $v=1$ mm/s giving a carrier frequency $v=2v/\lambda_0=2.4$ kHz. To form two-dimensional images, a longitudinal scan is recorded after each 10 microns of lateral displacement of sample 32. A 4 millimeter diameter beam, focused on sample 32 by lens 30 gave a 14 micron beam waste diameter. In air, sample arm 20 was matched in length to reference arm 18 at a position 200 microns past the focal point of lens 30, leading to a matched length in the beam focus of approximately 400 microns deep into sample 32 with a refractive index of 1.4. Detector 36 was AC coupled with signal amplified, highpass filtered at 1 kHz with 18 dB per octave roll-off and digitized with 16 bit resolution at 50 k points per second.

Signal processing was comprised of the steps of squaring the detected signal and phase sensitive demodulation with respect to $\dot{\Theta}t$ to separate the horizontal $I_H$ and vertical $I_V$ components of the backscattered light. Subsequently within each longitudinal scan, data points were averaged with a Gaussian weight function (FWHM=700 data points), to form one image pixel. The resulting signals gave the backscatted horizontal and vertical intensities as a function of z with a resolution of 10 $\mu$m physical distance, modulated with their respective birefringence dependent terms given by equation 3 below.

$$I_H(z)\cos^2(k_0 z\delta);\ I_V(z)\sin^2(k_0 z\delta); \quad 3$$

Figure 2A:
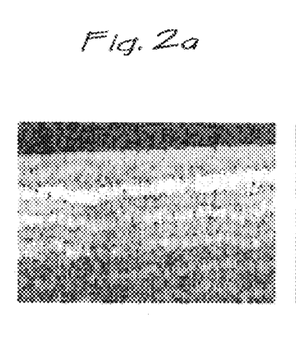
FIG. 2a is a birefringence image of fresh bovine tendon.

FIG. 2*a* is a birefringence image of fresh bovine tendon. In the illustrated embodiment below to demonstrate polarization sensitive optical coherence tomography, 1 mm wide by 700$\mu$ deep images of bovine tendon birefringence are shown and described before and after pulsed laser irradiation. It is to be expressly understood that the tomographic imaging technique of the invention is intended to be applied to any tissue or turbid medium. Measurements on a 1 cm samples at least 1 cm thick were done within 48 hours of sacrifice. The banded structure shown in FIG. 2*a* is indicative of birefringence and is clearly visible up to a physical depth of about 700 $\mu$m. The average refractive index of the tendon used in FIG. 2*a* was found to be 1.42±0.03 by measuring optical versus physical thicknesses of a thin slice. Birefringence was determined by measuring the average distance between the start or zero crossing between the first and second band over the full width of FIG. 2*a*, which was 100 lateral scans. The average distance $\bar{z}=116\pm13$ $\mu$m corresponds to a full period of sine squared in Eq. (3) above, $k_0\bar{z}\delta=\pi$. The measured birefringence $\delta$ was $3.7\pm0.4\times10^{-3}$ of bovine tendon which is predominantly a type I collagen, which is in good agreement with reported values of $3.0\pm0.6\times10^{-3}$ and $2.8-3.0\times10^{-3}$. The fit of an exponential $e^{-2z/\gamma}$, between $z=150-600$ $\mu$m depth to a total backscattered intensity in the sample 32, $I_b(z)$, averaged over the image of FIG. 2 gives $\gamma$ approximately equal to 0.2 millimeters, where $\gamma$ is the optical penetration depth. Decay of total backscattered light intensity with depth depends on several factors, among them attenuation of the partially coherent beam by scattering and geometry of the collection optics.

Figure 2B:
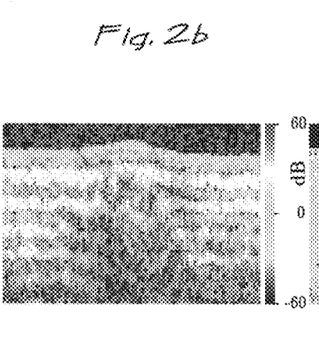
Figure 2C:
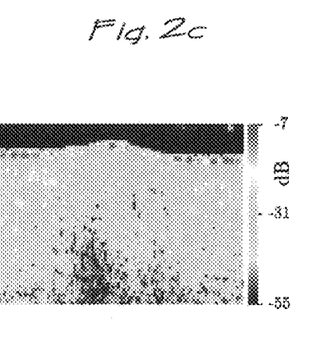
FIG. 2c is a conventional light optical coherence tomography of the bovine tendon of FIGS. 2a and b.

Each pixel in FIGS. 2*a–c* represents an area of 10×10 microns$^2$. In FIGS. 2*a* and *b* false color images were generated by computing $\text{sgn}[I_H(z)-I_V(z)]$ 10 $\log\ |I_H(z)-I_V(z)|$. Positive values were colored green-yellow, lower signals graded to red, negative values were colored green-blue and lower signals graded to deep blue. In FIG. 2*c* false color images were generated by computing 10 $\log\ |I_H(z)+I_V(z)|$, which were colored red-yellow to green-blue for lower signals over a dynamic range of 48 dB. A gray grayscale conversion has been made of the false color grading of FIGS. 2*a–c* for the purposes of the patent specification.

FIG. 2*b* is a computer tomograph birefringence of laser radiated bovine tendon shown in FIG. 2*a*. The image of FIG. 2*b* clearly shows a decrease in the birefringence of the center of the radiation zone which is in the center of the image extending into the tendon over the full depth of the image of 700 $\mu$m. Furthermore, the direction of incoming laser light from the upper left corner at an angle of 35° with respect to the normal surface is observable in the image of FIG. 2*b*. Surface temperature of the tendon was monitored during laser radiation using infrared radiometry. By comparison in FIG. 2*c* an optical coherence tomographic image of the total backscattered intensity $I_b(z)$ is shown. Although less backscattered light from the irradiated area is observable, the polarization sensitive image shown in FIG. 2*b* reveals important structural information which is clearly not shown in the conventional prior art optical coherence tomograph of FIG. 2*c*.

Figure 4:
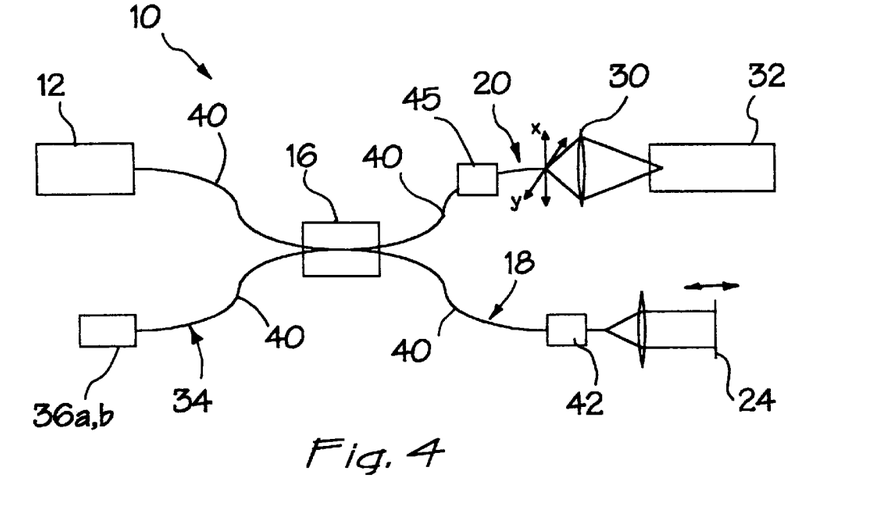
FIG. 4 is a diagram of a third embodiment of the apparatus of either FIGS. 1 or 3 where the optical paths are provided not in free space, but through optical fibers.
Figure 5A:
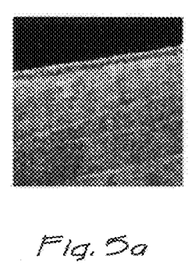
FIG. 5a is a digital graphic depiction of the Stokes vector I, for a sample of skeletal rat muscle derived from experimental data.
Figure 5B:
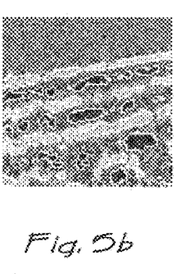
FIG. 5b is a digital graphic depiction of the Stokes vector Q, for the sample of skeletal rat muscle of FIG. 5a derived from experimental data.
Figure 5C:
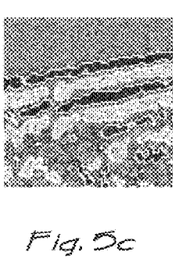
FIG. 5c is a digital graphic depiction of the Stokes vector U, for the sample of skeletal rat muscle of FIG. 5a derived from experimental data.
Figure 5D:
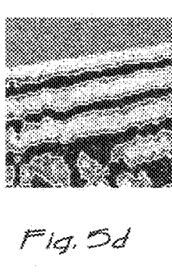
FIG. 5d is a digital graphic depiction of the Stokes vector V for the sample of skeletal rat muscle of FIG. 5a derived from experimental data.
Figure 5E:
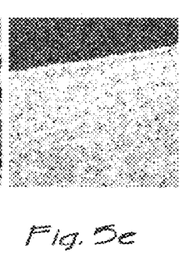
FIG. 5e is a digital graphic depiction of the degree of polarization P for the sample of skeletal rat muscle of FIG. 5a derived from experimental data.

FIG. 4 shows a schematic diagram of an implementation using polarization preserving optical fibers. The apparatus of FIG. 4 differs from that shown in FIGS. 1 and 3 in that in additional to the optical paths being defined within polarizing preserving optical fibers 40, a polarization modulator 42 provided is provided in reference arm 18 or may be placed in the sample arm. A phase modulator 45 is shown in sample arm 20, but may be alternatively placed in reference arm 18 if desired. Modulator 42 is an electro-optical device that rotates the polarization of the light in a controlled manner upon double passage through modulator 42. Rotating the polarization of the light in reference arm 18 in a linear or non-linear manner permits detection of two independent polarization states of light backscatted from tissue 32. Planar mirror 24 may be replaced by a corner cube or cat's eye retroreflector if desired. Thus, the polarization state of light backscattered from tissue 32 is determined after demodulation of the interference fringe intensity signal at detector 36*a* and *b*. The demodulation technique described is a specific example of particular methodology and is not intended to be general description. In particular, the polarization modulation frequency is higher than the carrier frequency resulting from the optical path length reference and sample arm modulation. Digital data acquisition and processing permits the independent determination of the phase and amplitude of the two independent polarization states of remitted backscattered light from tissue 32. Summing of the amplitude of the orthogonal polarized light signal fringes permits the determination of the total remitted backscattered light independent of the polarization state. A notable improvement over existing devices is that the indicated modulation technique is simpler and permits the use of a single light detector without the need of a beam splitter.

Consider now how polarization sensitive optical coherence tomography is used to determine the spatially resolved Stokes parameters of light backscattered from highly scattering biological samples. Changes in the Stokes parameters due to the optical phase delay between light propagating along the fast and slow axis of birefringence is measured through simultaneous detection of amplitude and relative phase of signal fringes and othoginal polarization states in the backscattered light formed by interference of light backscatted from biological sample 32 in sample arm 20 and from mirror 24 in reference arm 18.

The method can also be applied to the investigation of birefringence and highly scattering materials of any nature including ceramics and crystals. In contrast to the prior art where only the amplitude of the signal fringes in two othoginal polarization states was used, the present invention incorporates the phase relationship between interference fringes in each polarization channel to completely characterize the polarization state of light backscattered from the sample. Depth resolved changes in the Stokes parameters of light backscattered from sample 32 allow better understanding of the spatial variation in the sample birefringence and corresponding structural properties.

Consider now the signal developed in the device of FIG. 3 which was described above. Two dimensional images have formed of sample 32 in the device of FIG. 3 by lateral movement to sample 32 at 1 mm per second in the x direction which is repeated after each 10 $\mu$m incremental longitudinal displacement in the z direction, which is the direction of propagation of light. Active beam focus tracking in sample 32 was achieved by translating a piezoelectric transducer retroreflector assembly 43 after each transverse scan. The interference fringe carrier frequency of about 6 kHz was generated by modulating optical path lengths of reference arm 18 over about 20 $\mu$m with a 50 Hz triangular waveform driving assembly 43. An image pixel is calculated using the interference signal recorded over the central 10 $\mu$m of the reference arm modulation. Transverse and longitudinal pixel dimensions in the images were 10 $\mu$m by 10 $\mu$m.

To derive the expression of the Stokes parameters of the light in sample arm 20 in terms of the amplitude and relative phase of the interference fringes in othogonal polarization states, the electric fields are represented in the complex analytical form $E(z)=\int \tilde{e}(k)\exp(-ikz)dk$ with $k=2\pi/\lambda$ and $\tilde{e}(k)=0$ if $k<0$ where $\tilde{e}(k)$ is the wave field spectral amplitude. From the Wiener-Khinchine theorem, it follows that $<\tilde{e}^*(k)\tilde{e}(k')>=S(k)\delta(k-k')$, with $\delta(k-k')$ the Dirac delta function, and $S(k)$ the spectral density of a source. Since light from the reference arm was split equally into the horizontal and vertical polarization states, the electric field in reference arm is given by Eq. (4) below.

$$E_{x,y}(z_r) = \int_{-\infty}^{\infty} \tilde{e}(k)\exp(-2ikz_r)dk \quad \text{Eq. 4}$$

with $z_r$ the length of the reference arm 18. Electric field and sample arm 20 is given by Eq. (5) below.

$$\vec{E}(z_s) = \int_{-\infty}^{\infty} \sqrt{R(z_s)}\,\vec{a}(k,z_s)\tilde{e}(k)\exp(-2ikz_s)dk \quad \text{Eq. 5}$$

with $\sqrt{R(z_s)}$ describing the reflectivity at $z_s$ and the decay of the coherent beam in sample 32 and $\vec{a}(k,z_s)$ being the normalized complex vector amplitude of the polarization state of the light that was backscattered at depth $z_s$ with $\vec{a}^*(k,z_s)\cdot\vec{a}(k,z_s)=1$. The measured phase information is included in the normalized complex vector amplitude, $\vec{a}(k,z_s)$. The Stokes parameters, I, Q, U and V, of the electric field are calculated to be given by equations 6 and 7 below.

$$I(z_s) = R(z_s)\int [a_x^*(k,z_s)a_x(k,z_s) + a_y^*(k,z_s)a_y(k,z_s)]S(k)dk \quad \text{Eq. 6}$$

$$Q(z_s) = R(z_s)\int [a_x^*(k,z_s)a_x(k,z_s) + a_y^*(k,z_s)a_y(k,z_s)]S(k)dk$$

$$U(z_s) = R(z_s)\int 2Re[a_y^*(k,z_s)a_x(k,z_s)]S(k)dk$$

$$V(z_s) = R(z_s)\int 2Im[a_y^*(k,z_s)a_x(k,z_s)]S(k)dk$$

The interference intensity between light and sample path 20 and reference path 18 is given by equation 7.

$$\vec{I}(z_s, 2k) = \frac{1}{2\pi}\sqrt{R(z_s)}\,\vec{a}(k,z_s)S(k) \quad \text{Eq. (7)}$$

where $\Delta z = z_s - z_r$. The Fourier transform of $\vec{I}(z_s,\Delta z)$ with respect to $\Delta z$ is given by equation 8.

$$\vec{I}(z_s, 2k) = \frac{1}{2\pi}\sqrt{R(z_s)}\,\vec{a}(k,z_s)S(k) \quad \text{Eq. 8}$$

Using equation 8 in the Stokes parameters in equations 7 expressed in terms of the Fourier transform by equation 9.

$$I(z_s) = (2\pi)^2 \int \left[\vec{I}_x^*(z_s,2k)\vec{I}_x(z_s,2k) + \vec{I}_y^*(z_s,2k)\vec{I}_y(z_s,2k)\right]/S\,dk \quad \text{Eq. 9}$$

-continued $$Q(z_s) = (2\pi)^2 \int \left[ \tilde{I}_x^*(z_s, 2k)\tilde{I}_x(z_s, 2k) + \tilde{I}_y^*(z_s, 2k)\tilde{I}_y(z_s, 2k) \right] / S dk$$

$$U(z_s) = (2\pi)^2 \int 2Re\left[ \tilde{I}_y^*(z_s, 2k)\tilde{I}_x(z_s, 2k) \right] / S dk$$

$$V(z_s) = (2\pi)^2 \int -2Im\left[ \tilde{I}_y^*(z_s, 2k)\tilde{I}_x(z_s, 2k) \right] / S dk$$

It is to be expressly understood that many other formulas or algorithms exist for derivation of the Stokes parameters than those listed above. Therefore, the invention is not limited to the particular computational approach to the Stokes parameters which is discussed above, but explicitly includes all known or later derived methods for their derivation. The signals $I_x$ ($z_s$, $\Delta z$) and $I_y$ ($z_s$, $\Delta z$) are bandpass filtered between 3 and 10 kHz and digitized at $5\times10^4$ points per second each. For each pixel in an image, the Fourier transform of the central 10 $\mu$m are 256 points of the reference arm modulation is taken and digitally bandpass filtered between 5 and 7 kHz. The Stokes parameters for each pixel are calculated according to equation 9 with the spectral density of estimated by S(k) proportional to $$\left| \tilde{I}(z_s, 2k) \right| = \frac{1}{2\pi} \sqrt{R(z_s)} S(k).$$

$$Q(z_s) = (2\pi)^2 \int \left[ \tilde{I}_x^*(z_s, 2k)\tilde{I}_x(z_s, 2k) + \tilde{I}_y^*(z_s, 2k)\tilde{I}_y(z_s, 2k) \right] / S dk$$

$$U(z_s) = (2\pi)^2 \int 2Re\left[ \tilde{I}_y^*(z_s, 2k)\tilde{I}_x(z_s, 2k) \right] / S dk$$

$$V(z_s) = (2\pi)^2 \int -2Im\left[ \tilde{I}_y^*(z_s, 2k)\tilde{I}_x(z_s, 2k) \right] / S dk$$

To determine the polarization state reflected from the sample, the Stokes vectors need to be multiplied by the inverse of the Mueller matrix associated with quarter wave plate 28 in sample arm 20 with I↦I, Q↦−V, U↦U and V↦U. I is the backscattered intensity summed over both polarization channels. Q and U characterize linear polarization in frames rotated over 45° with respect to each other. The signs of Q and U indicate a predominant linear polarization and either of two othoginal planes. V describes circular polarization. The sign of V denotes the handedness. The Stokes parameters, I, Q, U and V satisfy the relationship, $I^2 \geq Q^2 + U^2 + V^2$ and a parameter $$P = \sqrt{(Q^2 + U^2 + V^2)/I}$$

can be defined that ranges from 0 to 1 and describes the degree of polarization.

Tomographic images of the Stokes parameters were formed by grayscale coding the common log of I from 0 to −48 dB where the 0 dB level corresponded to the maximum signal in an image. The polarization state parameters Q, U and V were grayscale coded by normalizing on the intensity I from −1 to 1 and P from 0 to 1. Contour lines indicating −⅓ and +⅓ fractions of the normalized parameters, Q, U and V were calculated after low pass filtering by convolving the images with a Gaussian filter of 4×4 pixels and overlaid with an original image.

FIGS. 5a–d and 6a–e show the four Stokes parameters measured in an ex vivo rat skeletal muscle and bone, respectively. The image of the Stokes parameter V is similar to that obtained by grayscale coding the birefringence induced phase retardation $$\phi = \arctan\sqrt{I_x^2(z)/I_y^2(z)} = k_o z \delta$$

with the exact relationship being V=cos 2ø.

The birefringence in FIG. 5 is attributed to the high structural order or anisotropy of skeleton muscle fibers. Several periods of Q, U and V, cycling back and forth between 1 and −1 are observed. FIG. 5a is a depiction of I, FIG. 5b a depiction of Q, FIG. 5c a depiction of U, FIG. 5d a depiction of V and FIG. 5e the degree of polarization P. The birefringence was determined by measuring the distance of a full period of V which corresponds to a phase retardation of $\pi = k_o z \Delta 2.4 \times 10^{-3}$. The greater birefringence in skeletal muscles compared to myocardium has been attributed to the structural differences between these two different types of muscle. The myocardium muscles fibers are oriented in different directions and not necessarily parallel to the muscle surface. The skeletal muscle image in FIGS. 5a–5e shows a high degree of muscle fiber alignment, the orientation of which can be determined by finding the rotation of the reference frame that minimizes the variance in either Q or U and what resulted in an angle of −7° with respect to the vertical of one of the optical axis which is in good agreement with the fiber direction which was approximately perpendicular to the horizontal scan direction.

Figure 6A:
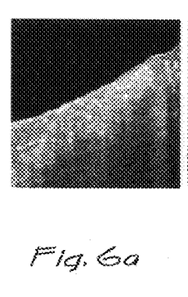
FIG. 6a is a digital graphic depiction of the Stokes vector I, for a sample of rat bone derived from experimental data.
Figure 6B:
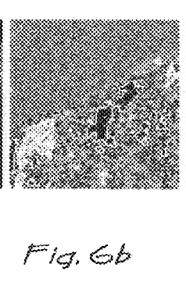
FIG. 6b is a digital graphic depiction of the Stokes vector Q, for the sample of rat bone of FIG. 6a derived from experimental data.
Figure 6C:
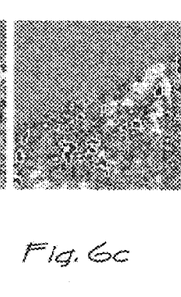
FIG. 6c is a digital graphic depiction of the Stokes vector U, for the sample of rat bone of FIG. 6a derived from experimental data.
Figure 6D:
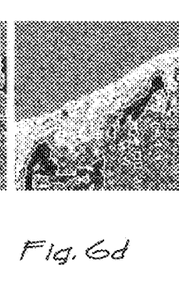
FIG. 6d is a digital graphic depiction of the Stokes vector V for the sample of rat bone of FIG. 6a derived from experimental data.
Figure 6E:
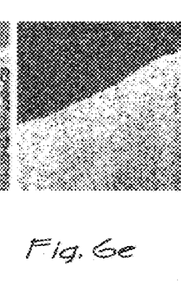
FIG. 6e is a digital graphic depiction of the degree of polarization P for the sample of rat bone of FIG. 6a derived from experimental data.

The birefringence depicted in FIGS. 6a–6e also depicting the Stokes parameters I, Q, U, V and the degree of polarization P respectively, is attributed to the presence of collagen. The V parameter image of FIG. 6d shows an apparent loss of birefringence. However, the Q parameter image of FIG. 6b reveals that the predominant orientation of the linear polarization in either of the two othoginal planes is reversed around the region showing the apparent loss of birefringence. This indicates that in the region showing loss of birefringence in FIG. 5d, there is a transition of a dominant orientation of the optical axis.

Therefore, a determination as shown in FIGS. 5a–5e and 6a–6e of examples of the spatially resolved Stokes parameters of light reflected from turbid sample 32 reveals substantial additional structural information than was previously obtainable by prior art methods that used only the intensity in two orthogonal polarization channels. In samples with a constant orientation of the optical axes, birefringence and the orientation of the optical axes can be determined. Parameter, P, reveals information on a multiply scattered light in optical coherence tomographic images through the decrease of the degree of polarization. An analysis of the evolution of the Stokes parameters in a biological sample allows determination of the changes and birefringence and in the orientation of the optical axis and turbid samples during radiative mediation.

Figure 7:
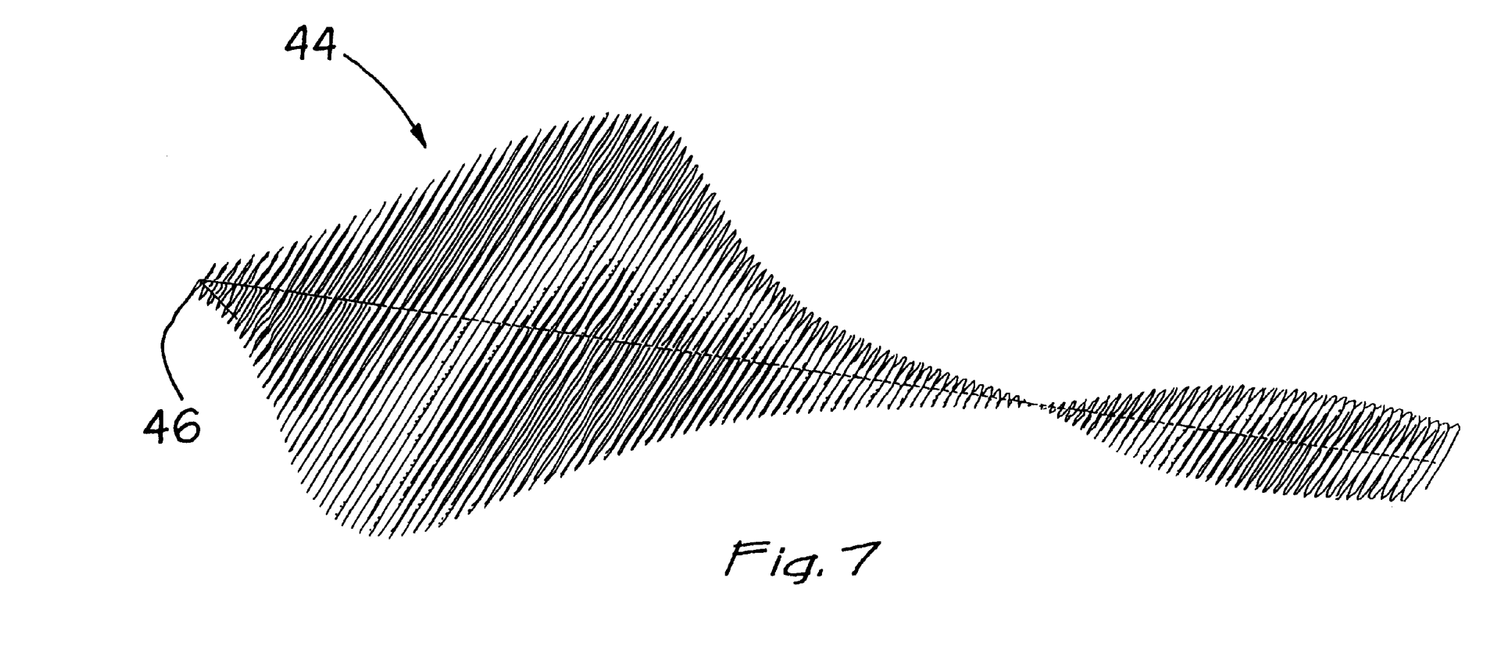
FIGS. 7, 7a and 7b are digital graphs of data showing the spatial evolution of the polarization of the E wave in rat muscle derived from experimental data.
Figure 7A:
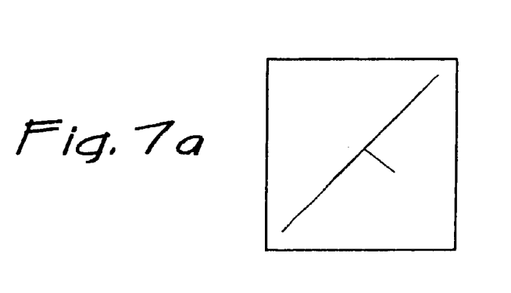
Figure 7B:
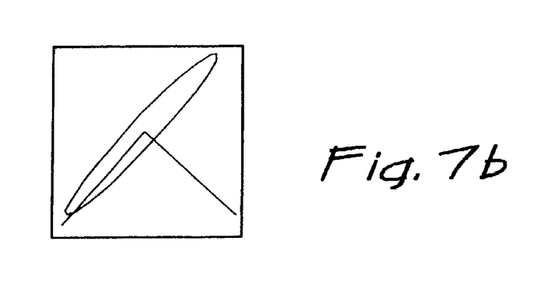

FIG. 7, 7a and 7b are a digital graphs of data showing the evolution of a reflected light propagating through the birefringent murine muscle as seen in the detection arm of apparatus 10 of the invention. The electromagnetic wave is reconstructed in FIG. 7 from the horizontal amplitude $A_H$ and the vertical amplitude $A_V$ polarized components and relative phase of the interference fringes detected in the device of FIG. 3. The evolution of the wave shown in FIG. 7 is a small section of the longitudinal scan taken from the middle of an image of murine muscle. The length of the section of the scan depicted in FIG. 7 is 38 μm within sample 32 in which a sample refractive index of 1.4 is realized. The initial portion 44 of the scan shown on FIG. 7 is the reflection from the sample surface modulated by the coherence envelope.

Inserts FIG. 7a and 7b are cross-sectional diagrams of the electromagnetic wave taken over full cycle in a direction perpendicular to the propagation at 5.7 and 35.7 μm from beginning 46 of the section scan. As FIG. 7 graphically depicts as interpreted by insets FIGS. 7a and 7b, the initial polarization is linear along one of the displayed axis and changes to an elliptical polarization state as shown in FIG. 7b deeper within the tissue sample 32.

Figure 8:
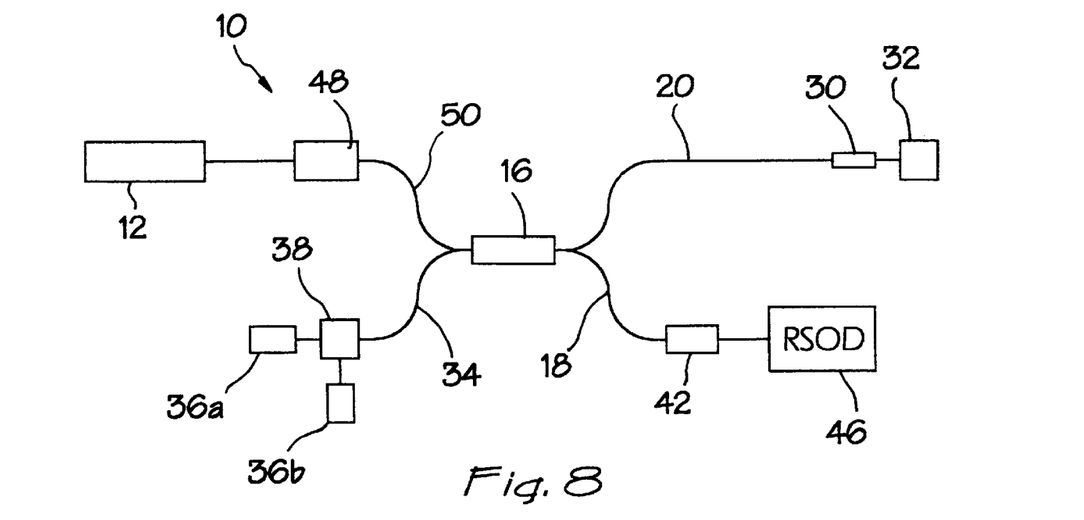
FIG. 8 is a third embodiment of the invention that employs a rapid spectral optical delay line to allow a longitudinal scan speed and modulation frequency or Doppler shift to be set independently.

In the third embodiment of FIG. 8 apparatus 10 employs two detectors 36a and 36b and the detection 34 of Michelson interferometer 10 to detect to orthogonal polarization states. Apparatus 10 allows measurement of the changes of polarization state and the intensity with high spatial resolution of between 1 to 10 μm and high sensitivity, greater than 100 dB, of light that is backscattered from a transparent or turbid medium or sample 32. The information is used to determine birefringence and the optical axes of birefringence or optical activity and transparent and turbid media for use in biomedical imaging, or to determine stress or lattice deformation or other structural information in materials such as crystals and ceramics.

Apparatus 10 of FIG. 8 does not employ polarization preserving fibers. Modulation of the input polarization state incident on sample 32 is at an arbitrary frequency. Data processing algorithms allow the optical axis and birefringent nature of the sample to be determined, because at any location inside sample 32 sample-induced changes in both the linear and circular polarization are measured. The embodiment of FIG. 8 employs a rapid spectral optical delay line 46 that allows a longitudinal scan speed and modulation frequency or Doppler shift to be set independently. This is achieved by placement of a fiber optic phase modulator in either reference arm 18 or sample arm 20 of interferometer 10. In the illustration in FIG. 8 phase modulator 42 is shown in reference arm 18.

Light source 12 of FIG. 8 has low temporal and high spatial coherence. Source 12 can either be polarized in a single state or can be polarized by polarizer and wave plates in an arbitrary single state. An aiming beam of visible light can be combined with light source 12 if desired. Polarization modulator 48, such as an eletrooptic wave plate(s) or other equivalent device(s) or combination of devices, modulates the pure polarization state to map out part of or, with a combination of polarization devices, the complete Poincare sphere which completely describes the polarization state of light. Polarization modulator 48 is placed either in light source arm 50 or sample arm 20. As a result, the input polarization state of light incident upon sample 32 samples part of or the complete Poincare sphere. Since each spatial location of sample 32 is probed with a complete set of polarization states, the local optical axes of birefringence can be determined.

Rapid spectral optical delay line 46 of FIG. 8 is used as a longitudinal or depth scanning mechanism and is known in the art as described by G. J. Tearney, et al. Opt. Lett. 22, 1811 (1997). Rapid spectral optical delay line 46 is modified by adding a phase modulator 42 in reference arm 18. The advantage of phase modulator 42 and reference arm 18 is a decoupling of the longitudinal scan speed in the modulation frequency or Doppler shift of rapid spectral optical delay line 46. Phase modulator 42 modulates optical length to reference arm 18 within a few wave lengths. Phase modulator 42 can be driven by any one of several different types of waveforms, such as sawtooth, triangular, sinusoidal or a combination of sinusoids. Although the sawtooth and triangular waveforms are the simplest driving signals to implement, driving phase modulator 42 with a special combination of sinusoids, such as a fundamental frequency and higher harmonics, allows demodulation of the signal at the fundamental frequency while phase information is preserved. The improved quality of frequency modulated signal at detectors 36a and 36b allows for better determination of the polarization state of the light. In addition, it improves the quality of Doppler flow velocity analysis of the signal.

Figure 8A:
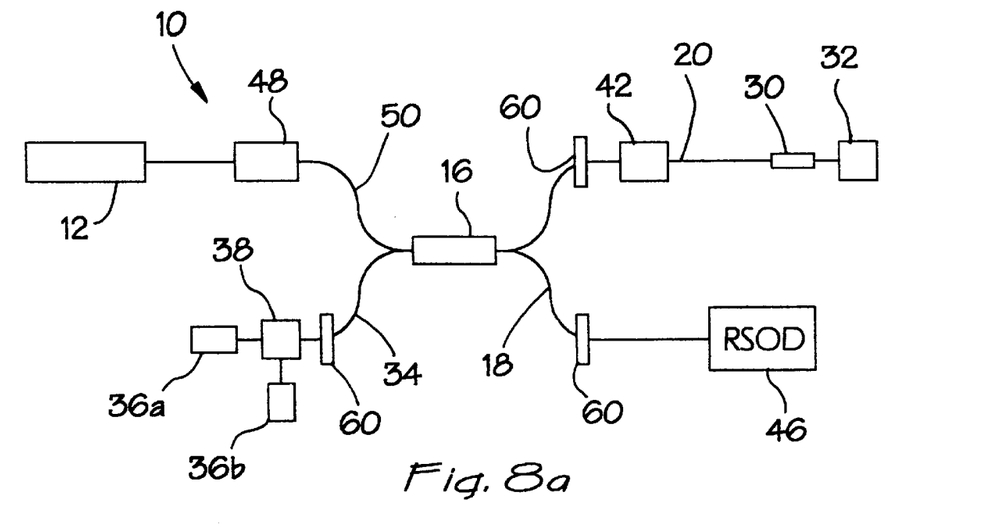
FIG. 8a is schematic diagram of a fourth embodiment of the invention similar to that shown in FIG. 8, except the phase modulator is disposed in the sample arm instead of the reference arm.
Figure 8B:
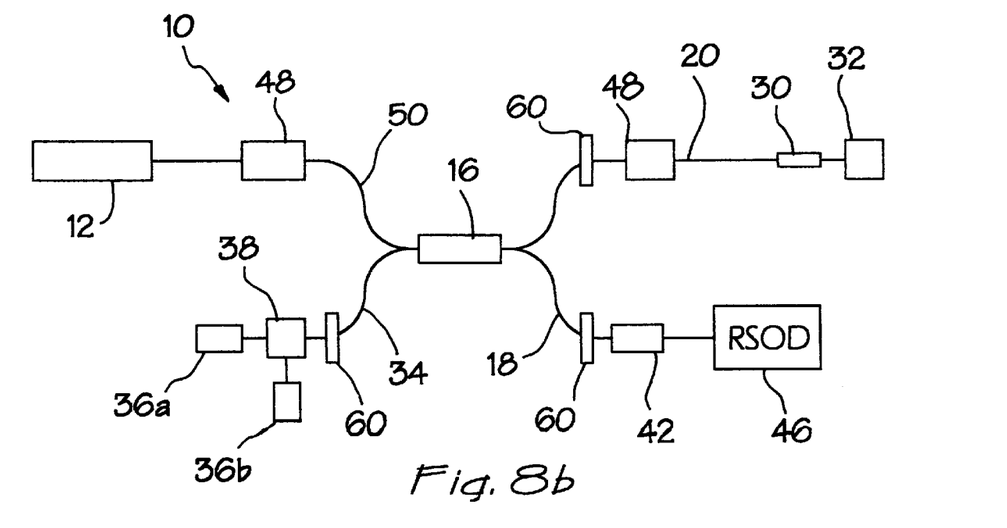
FIG. 8b is schematic diagram of a fifth embodiment of the invention similar to that shown in FIG. 8, wherein the phase modulator is moved from the source arm to the sample arm, or alternatively a second phase modulator is disposed in the sample arm instead of the reference arm.

In detection arm 34 of inferometer 10 of FIG. 8 a polarizing beam splitter 38 separates the detected light into two othoginal polarization states before being detected. Throughout the design, static polarization controllers can be added to manipulate the polarization into a desired state such as static quarterwave plates 60 shown in FIGS. 8a and 8b.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. An apparatus for polarization sensitive optical coherence tomography of a sample characterized by optical birefringence comprising:

an interferometer having a source arm, a reference arm, a sample arm and a detector arm;

a source of at least partially coherent polarized light coupled to said source arm, said partially coherent polarized light being characterized by a well defined polarization state;

a polarization modulator, wherein polarization modulated light is returned to said detector arm from said reference arm and wherein polarization modulated light is incident on said sample and arbitrarily polarized light is returned to said detector arm from said sample arm according to sample birefringence, said returned light from said reference arm and sample arm interfering in said detector arm to form polarization interference fringes; and a polarization demodulator to demodulate said polarization interference fringes to generate a complete polarization state description of said backscattered light from said sample by preserving phase relationships between orthogonal components of said polarization interference fringes formed from backscattered light from said sample and from said reference arm.

2. The apparatus of claim 1 further comprising a scanner for laterally moving said sample and said sample arm relative to one another transverse to the longitudinal direction along which said light is incident on said sample, and for longitudinally moving said sample and sample arm relative to one another to obtain a two dimensional image of said sample.

3. The apparatus of claim 1 wherein said polarization modulator circularly polarizes orthogonal states of said polarization modulated light.

4. The apparatus of claim 1 wherein said polarization demodulator comprises a single detector which detects polarization modulation of said polarization modulated light to obtain relative phase differences between orthogonal components of said polarization modulated light.

5. The apparatus of claim 1 wherein said polarization demodulator comprises two detectors, each of which detects over time a separate orthogonal component of said polarization modulated light to obtain a complete set of polarization states of the Poincare sphere sufficient to determine orientation of optical axes of said sample and birefringence of said sample.

6. The apparatus of claim 5 wherein said sample is characterized by a Mueller matrix as a full characterization of its optical polarization properties and wherein said complete set of polarization states of the Poincare sphere generated by said detectors are usable to compute said Mueller matrix of said sample.

7. The apparatus of claim 6 further comprising a computer for computing said Mueller matrix from said complete set of polarization states of the Poincare sphere generated by said detectors.

8. The apparatus of claim 1 wherein said polarization demodulator averages said demodulated, orthogonal polarization states of interference fringes according to a weighted average to obtain a value for a pixel image.

9. The apparatus of claim 1 wherein uniformly rotating linear polarized light is returned to said detector arm from said reference arm.

10. The apparatus of claim 9 wherein an uniformly rotating quarter wave plate rotates linearly polarized light in said reference arm.

11. The apparatus of claim 1 wherein nonuniformly rotating linear polarized light is returned to said detector arm from said reference arm.

12. The apparatus of claim 11 wherein a polarization modulator rotates linearly polarized light in said reference arm through at least part of the Poincare sphere.

13. The apparatus of claim 12 wherein said polarization modulator comprises an electro-optical variable waveplate.

14. The apparatus of claim 1 further comprising a rapid spectral optical delay line to provide for longitudinal scanning of said sample.

15. The apparatus of claim 14 further comprising a phase modulator in said sample arm to decouple longitudinal scan speed and modulation frequency of said rapid spectral optical delay line.

16. The apparatus of claim 14 further comprising a phase modulator in said reference arm to decouple longitudinal scan speed and modulation frequency of said rapid spectral optical delay line.

17. The apparatus of claim 1 wherein said demodulator generates the Stokes parameters, I, Q, U and V from said orthogonal signal components of the intensity of backscattered light from said sample.

18. The apparatus of claim 17 wherein said demodulator generates the degree of polarization, P, from said orthogonal signal components of the intensity of backscattered light from said sample.

19. The apparatus of claim 1 wherein said polarization interference fringes generate a carrier signal, and wherein said phase modulator generates an improved quality carrier signal by generating said carrier signal at a fundamental frequency and a plurality of harmonics of said fundamental frequency or at least one harmonic of said fundamental frequency whereby quality of Doppler velocity measurements is improved.

20. The apparatus of claim 1 wherein said source arm, reference arm, sample arm and detector arm comprise polarization preserving optic fibers.

21. The apparatus of claim 1 wherein said source arm, reference arm, sample arm and detector arm comprise single mode optic fibers.

22. The apparatus of claim 1 where said polarization modulator is disposed in said sample arm.

23. A method for performing polarization sensitive optical coherence tomography of a sample characterized by optical birefringence comprising:

providing a source of at least partially coherent light coupled to an interferometer having a source arm, a reference arm, a sample arm and a detector arm;

polarization modulating said light in at least said reference arm or sample arm;

returning said polarization modulated partially coherent light to said detector arm from said reference arm and said sample arm, said polarization modulated partially coherent light being incident on said sample and arbitrarily polarized light being returned to said detector arm from said sample arm according to sample birefringence, said returned light from said reference arm and sample arm interfering in said detector arm to coherently gate said returned light from said sample arm in said detection arm to select between a multiplicity of optical paths of backscattered light returned from said sample arm to form polarization interference fringes; and demodulating said polarization interference fringes in said detector arm combined from light returned from said reference arm and from said sample arm to provide a data signal indicative said optical birefringence of said sample.

24. The method of claim 23 where providing said source of polarization modulated partially coherent light coupled to an interferometer comprises uniformly rotating said linearly polarized partially coherent light in said reference arm or sample arm.

25. The method of claim 23 where providing said source of polarization modulated partially coherent light coupled to an interferometer comprises nonuniformly rotating said linearly polarized partially coherent light in said reference arm.

26. The method of claim 23 where demodulating phase sensitive, orthogonal polarization states of interference fringes in said detector arm combined from light returned from said reference arm and from said sample arm to provide a data signal indicative said optical birefringence of said sample further comprises generating the Stokes parameters, I, Q, U and V from said orthogonal signal components of the intensity of backscattered light from said sample to provide a complete polarization state description of said backscattered light from said sample.

27. The method of claim 26 further comprising laterally scanning said sample transverse to the longitudinal direction along which said light is incident on said sample, and longitudinally scanning said sample to obtain a two dimensional image of said sample.

28. The method of claim 23 wherein demodulating said polarization modulated interference fringes is performed using two detectors, each of which detects over time a separate orthogonal component of said polarization modulated light to obtain a complete set of polarization states of the Poincare sphere sufficient to determine orientation of optical axes of said sample and birefringence of said sample.

29. The method of claim 28 wherein said sample is characterized by a Mueller matrix as a full characterization of its optical polarization properties and wherein demodulating said polarization modulated interference fringes using two detectors generates said complete set of polarization states of the Poincare sphere usable to compute said Mueller matrix of said sample.

30. The method of claim 29 further comprising computing said Mueller matrix from said complete set of polarization states of the Poincare sphere generated by said detectors.

31. The apparatus of claim 23 wherein said polarization interference fringes generate a carrier signal, and wherein said phase modulator generates an improved quality carrier signal by generating said carrier signal at a fundamental frequency and a plurality of harmonics of said fundamental frequency or at least one harmonic of said fundamental frequency whereby quality of Doppler velocity measurements is improved.

32. A method for performing polarization sensitive optical coherence tomography of a sample characterized by optical birefringence comprising:

generating two polarization-modulated orthogonal polarization states of an at least partially coherent light signal;

generating interference fringes of two polarization-modulated orthogonal polarization states from a reference signal and a backscattered sample signal, said fringes having an amplitude and relative phase with respect to said other modulated orthogonal polarization state for each of said two polarization-modulated orthogonal polarization states;

measuring said amplitude and phases of said interference fringes of said two polarization-modulated orthogonal polarization states; and polarization demodulating said amplitude and phases of said interference fringes of said two polarization-modulated orthogonal polarization states to obtain the full polarization state of said backscattered sample signal to obtain structural information pertaining to said sample.

33. The method of claim 32 where demodulating said amplitude and phases of said interference fringes comprises generating Stokes parameters, I, Q, U, and V, and generating said structural information from said Stokes parameters.

* * * * *